US00PP15286P2

(12) United States Plant Patent
van Dijk

(10) Patent No.: US PP15,286 P2
(45) Date of Patent: Nov. 2, 2004

(54) ***ANTHURIUM ANDREANUM* PLANT NAMED 'ANTHBNEQ'**

(50) Latin Name: *Anthurium andreanum L.*
Varietal Denomination: Anthbneq

(75) Inventor: Jan van Dijk, Bleiswijk (NL)

(73) Assignee: Anthura B.V. (NL)

( * ) Notice: Subject to any disclaimer, the term of this patent is extended or adjusted under 35 U.S.C. 154(b) by 0 days.

(21) Appl. No.: 10/612,051

(22) Filed: Jul. 3, 2003

(51) Int. Cl.[7] ..... A01H 5/00
(52) U.S. Cl. ..... Plt./365
(58) Field of Search ..... Plt./365

(56) References Cited

FOREIGN PATENT DOCUMENTS

EM 11621 8/2003

OTHER PUBLICATIONS

UPOV–ROM GTITM Computer Database 2003/05, GTI Jouve Retrieval Software, Citation for 'Anthbneq'.*
European Community Plant Breeder's Rights Application No. 2001/1321 Technical Examination, May 15, 2003.
European Community Plant Breeder's Rights Official Gazette Dec. 15, 2001.
European Community Plant Breeder's Rights Application No. 2001/1321, Aug. 8, 2001.

* cited by examiner

*Primary Examiner*—Anne Marie Grunberg
*Assistant Examiner*—Annette H Para
(74) *Attorney, Agent, or Firm*—Foley & Lardner LLP

(57) ABSTRACT

A new and distinct cultivar of *Anthurium andreanum* plant named 'Anthbneq', as described and illustrated, and particular characterized by the combined features of compact growth and early and rich flowering; mini-type pot plant with large flowers, maximum growth to approximately 40 cm; long and erect peduncle; flowers held just above the foliage; full plant habit due to rich shoot formation and compactness of the plant; dark green leaves, durable and very glossy, with light green primary veins; red and durable flowers, slowly turning brownish-red with age; large amount of flowers in relation to the amount of leaves resulting in good leaf to flower ratio size.

4 Drawing Sheets

Latin name of the genus and species of the plant claimed: *Anthurium andreanum* L.
Variety denomination: Anthbneq.

BACKGROUND OF THE INVENTION

'Anthbneq' is a new and distinct cultivar of *Anthurium*, botanically known as *Anthurium andreanum* L. The new cultivar is a product of a planned breeding program, and was obtained from a cross made during such a program in Bleiswijk, The Netherlands, in 1996.

The female or seed parent was a pink-colored *Anthurium* pot plant identified as number 95-634-01 (unpatented). The male or pollen parent was an orange-colored flowering *Anthurium* pot plant identified as number 95-532-02 (proprietary, unpatented). 'Anthbneq' was discovered and selected as a flowering plant within the progeny of the stated cross by the inventor, Jan van Dijk, in March, 1998 in a controlled environment in a glasshouse in Bleiswijk, The Netherlands.

Subsequent asexual reproduction by tissue culture in Bleiswijk has demonstrated that the combination of characteristics as herein disclosed for the new cultivar are firmly fixed and are retained through successive generations of asexual reproduction.

BRIEF DESCRIPTION OF THE INVENTION

The following traits have been repeatedly observed and in combination distinguish 'Anthbneq' as a new and distinct cultivar:

1. Compact growth and early and rich flowering;
2. Mini-type pot plant with large flowers, maximum growth to approximately 40 cm;
3. Long and erect peduncle; flowers held just above the foliage;
4. Full plant habit due to rich shoot formation and compactness of the plant;
5. Dark green leaves, durable and very glossy, with light green primary veins;
6. Red and durable flowers, slowly turning brownish-red with age;
7. Large amount of flowers in relation to the amount of leaves resulting in good leaf to flower ratio size.

In comparison to the female parental cultivar, 95-634-01, 'Anthbneq' has larger spathes, red in color, whereas the spathes of the female parent are pink. 'Anthbneq' has larger, darker leaves than the female parent.

In comparison to the male parental cultivar, 95-523-02, 'Anthbneq' has more durable, smaller spathes, red in color, whereas the spathes of the male parent are orange. In addition, 'Anthbneq' grows more compact than the male parent.

BRIEF DESCRIPTION OF THE DRAWINGS

The accompanying photographs, taken in Bleiswijk, The Netherlands, show typical 'Anthbneq' specimens.

FIG. 1 is a side-view of 'Anthbneq' showing the flowers held well above the leaf canopy.

FIG. 2 is a close-up of a 'Anthbneq' flower showing the spathe and spadix with pollen.

FIG. 3 is a close-up of 'Anthbneq' flowers at three different development stages: from young on the left to old on the right. The youngest flower has an unripe spadix (pistils and pollen are not visible yet). The flower in the middle has a ripe spadix with sime pollen. The spathe of the old flower on the right becomes darker red. There is a difference in age of approximately 8 to 10 weeks between the flower depicted on the left and the flower depicted on the right.

FIG. 4 is a close-up of the top of a young (left) and old leaf blade (right) showing the difference between old and young leaf blades. It shows that the young leaf blades are more shiny then the old leaf blades.

DETAILED BOTANICAL DESCRIPTION

The following observations, measurements and values describe plants grown in Bleiswijk, The Netherlands, under greenhouse conditions, which closely approximate those generally used in horticultural practice. Color references are made to The Royal Horticultural Society (R.H.S.) Colour Chart, except where general color terms of ordinary significance are used. The color references are approximate, as color depends to a degree on horticultural practices such as light level and degree of fertilization, among others. The color values were determined between 11:00 a.m. and 3:00 p.m. on Mar. 25, 2003, under 5000 lux natural light in a glasshouse in Bleiswijk. The phenotype may vary significantly when grown under different conditions of temperature, light or other determining factors, without a change in genotype of the plant.

Propagation: Asexual propagation by means of tissue culture and all propagation that flowered have been true to the original type in plant and flower characteristics.

Plant description: Approximately 55–60 weeks following division, 'Anthbneq' will reach a mature size of approximately 35 cm to 40 cm in height and approximately 40 cm to 45 cm in width in a 17 cm container.

Leaves:

*Form.*—The leaf blade is elliptical-cordate with an acuminate tip and a cordate base. The leaf blade angle with the petiole is between 110 and 140 degrees. 'Anthbneq' makes larger leaf blades as it ages. 'Anthbneq' also produces some axillary shoots with small leaf blades. Therefore, a wide range in leaf blade length and width is found on each plant. The minimum leaf blade length is approximately 4 cm and the maximum leaf blade length is approximately 19 cm. The minimum leaf blade width is approximately 2 cm and the maximum leaf blade width is approximately 13 cm.

*Texture.*—The leaf blades are very shiny, leatherly and thick. The mature leaf blades are weakly cupped. The young leaf blades are more shiny then the old leaf blades.

*Veins.*—The mid-vein and primary veins (the veins which radiate out from the juncture of petiole and leaf) protude at the underside of the leaf blade. In older leaf blades (approximately more than 4 weeks), the green color of the veins at the upper surface (RHS 146B) and the lower surface (RHS 146D) of the mid-vein and primary veins contrast with the darker green color of the surface of the leaf blade.

*Leaf blade-color.*—Young leaf blade (approximately 3 to 3 weeks old) upper surface is dark green (RHS 147A) and lower surface is brown-grey (RHS 199B). The old leaf blade (approximately more than 4 weeks) upper surface is green (RHS 139A) and the lower surface is light green (RHS 146B).

*Lobes.*—A leaf blade has two small lobes extending past the petiole. The distance from the petiole and leaf juncture to the highest point on the lobes of mature leaf blades (width 8 cm, length 12 cm) ranges approximately from 3.5 to 4.5 cm.

*Petiole.*—The color of the petiole of an old leaf blade is green (RHS 147B). The petiole color of a young leaf blade is brown-red (RHS 199B). The cross section of a petiole is round and the diameter is approximately 4 to 5 mm. The color of the cataphyls surrounding the petioles is brown (RHS 165A) with a brown-red base (RHS 181C).

Spathe:

*Buds.*—The spathe is tightly rolled around the spadix and extrudes from the peduncle sheath. After the spathe is fully open the peduncle elongates for a few more centimeters.

*Size.*—The completely developed spathe of a 35 cm tall plant is approximately 10 cm to 12 cm long and approximately 9 cm to 10 cm wide.

*Color.*—When the spathe is just fully open the upper surface is red (RHS 45A) and the lower surface also red (RHS 46C). Approximately 14 to 16 weeks after opening, the spathe discolors to dark brown (RHS 200A). The red color slightly disappears. After approximately another 10 to 16 weeks the complete flower will die off.

*Arrangement.*—The spathe angle with the peduncle is between 90 and 110 degrees. The spathe stands on a straight wiry peduncle approximately 2 cm to 5 cm above the foliage. The peduncle cross-section is round and the diameter approximately 4 mm to 5 mm, depending on the age of the plant. The peduncle is erect and its length on the plant depends on the age. It ranges from approximately 15 to 30 cm.

*Shape.*—The spathe is ovate with a mucronate tip and a cordate base. A just fully opened spathe is slightly cup-shaped. The edges of the spathe stay upward.

Flowering time: One small untreated tissue culture plant of approximately 2 cm tall will flower, depending on season, after approximately 15 to 16 months when approximately 2 to 3 blossoms will appear. More blossoms appear some week so that a full flowering and salable plant can have 6 to 10 red flowers. Smaller blossoms may occur on less mature growth.

Reproductive organs:

*Size.*—The spadix measures approximately 3 to 5 cm in height. The length of the spadix is shorter than the length of the spathe. The spadix is a little columnar. The width of a mature spadix, that is approximately 5 cm long, is approximately 7 mm to 8 mm at the base and approximately 6 mm to 7 mm at the top. The spadix angle with spathe is approximately 50 to 70 degrees.

*Color.*—At the time the spathe unrolls the spadix is unripe. Later as the spadix matures, pistils become visible and pollen is produced. An unripe spadix is yellow (RHS 13A) and a ripe spadix is white. As the spadix matures (from base to tip) it becomes fully green. Berries exist on the spadix when pistils have been pollinated.

*Stamens.*—Anthers and filaments are not clearly visible on the spadix.

*Pollen.*—Some produced; white in color.

*Pistil.*—Unripe pistil is yellow (RHS 13A) and a ripe spadix is white. The pistil protrudes from the spadix.

*Berries.*—Number of berries after pollination ranges from 1 to 200; the size of the berries grows from 0.1 cm just after pollination to 0.4 cm after approximately 26 weeks; color is green, RHS 137 B (unripe), changing to brownish-yellow, RHS 169 B to 169 C (ripe); flower diameter is approximately 2 mm with up to 200 flowers existing on a fully grown spadix of 5 cm.

Roots: Pinkish-white roots with smaller hairy laterals. The root-tips are yellow.

Disease/pest resistance: No known resistance and/or susceptibility to diseases and pests.

I claim:

1. A new and distinct *Anthurium andreanum* plant named 'Anthbneq', as herein described and illustrated.

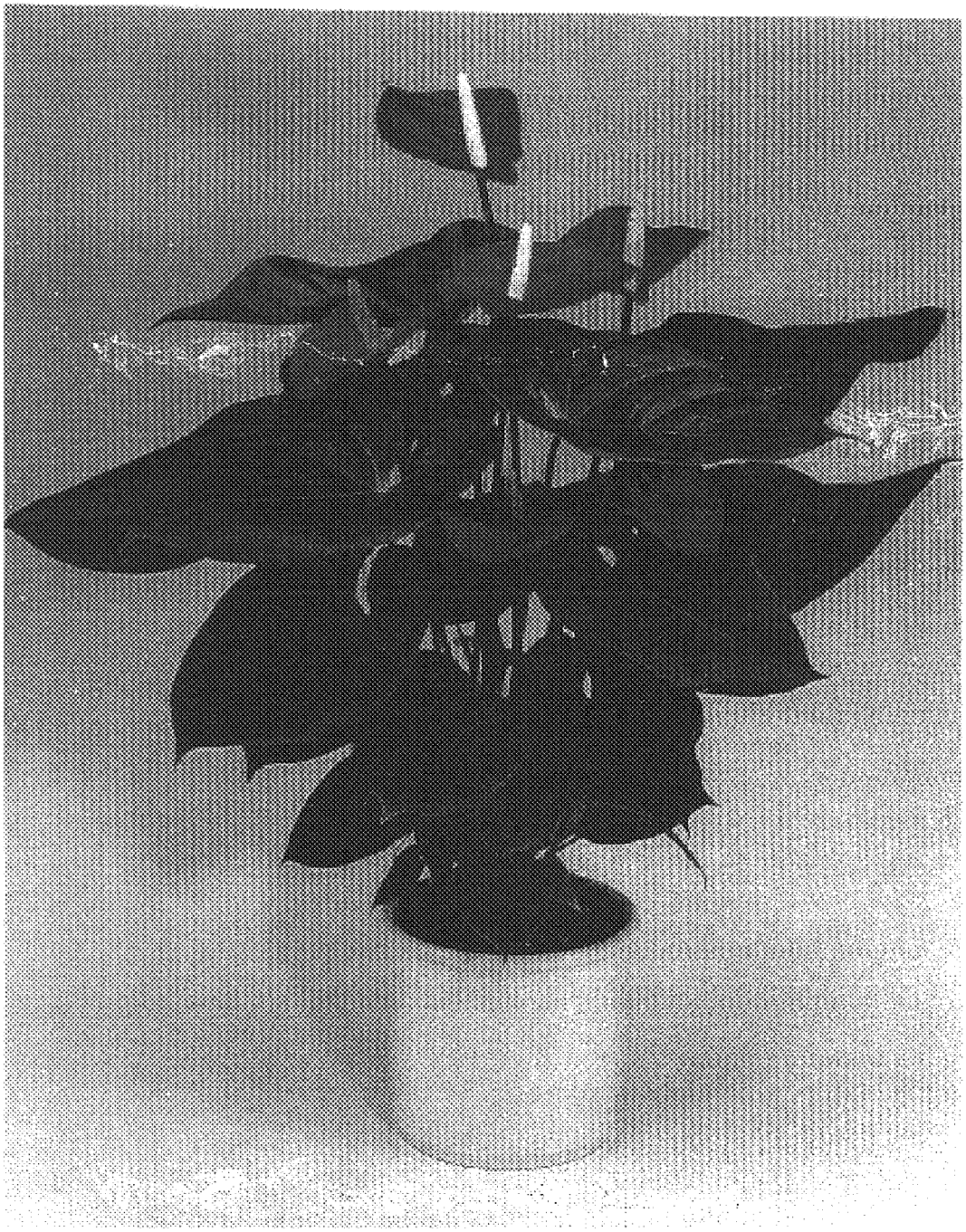

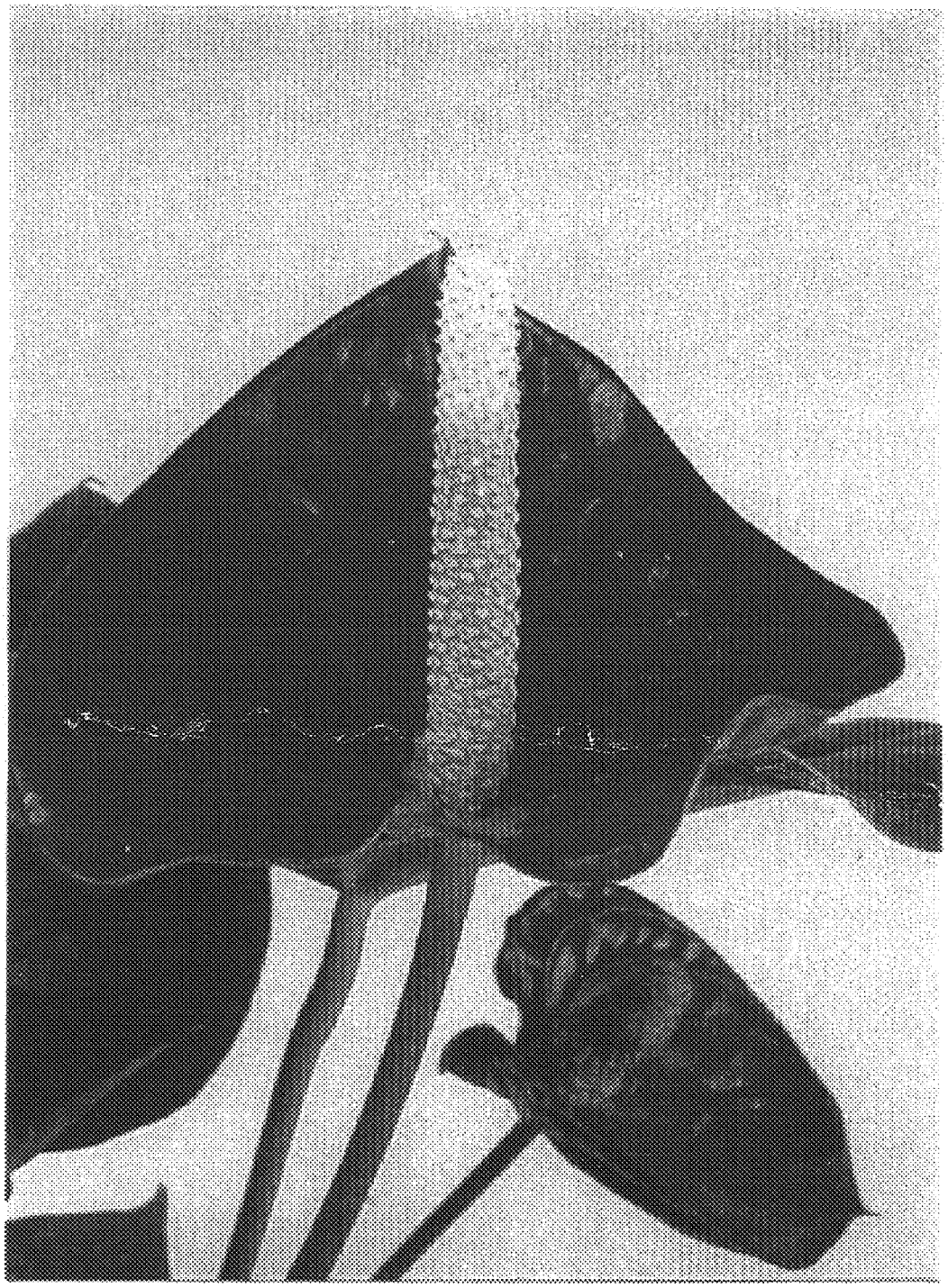

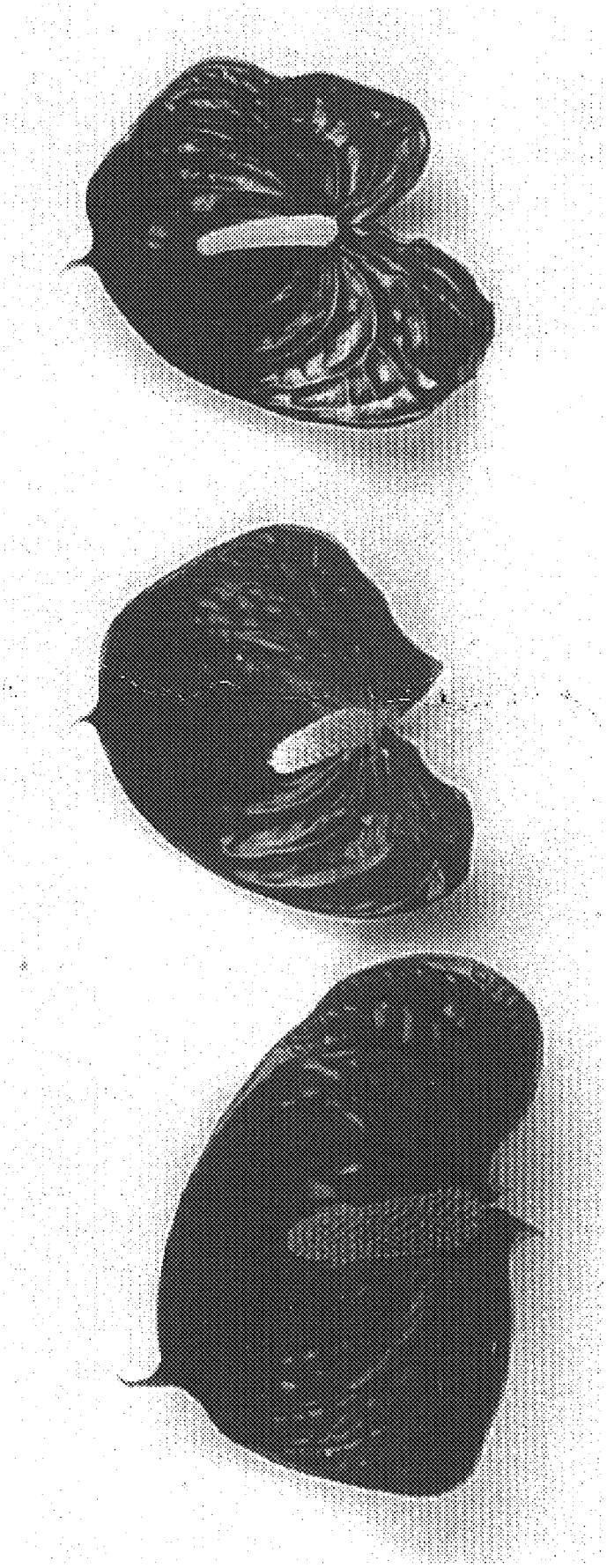

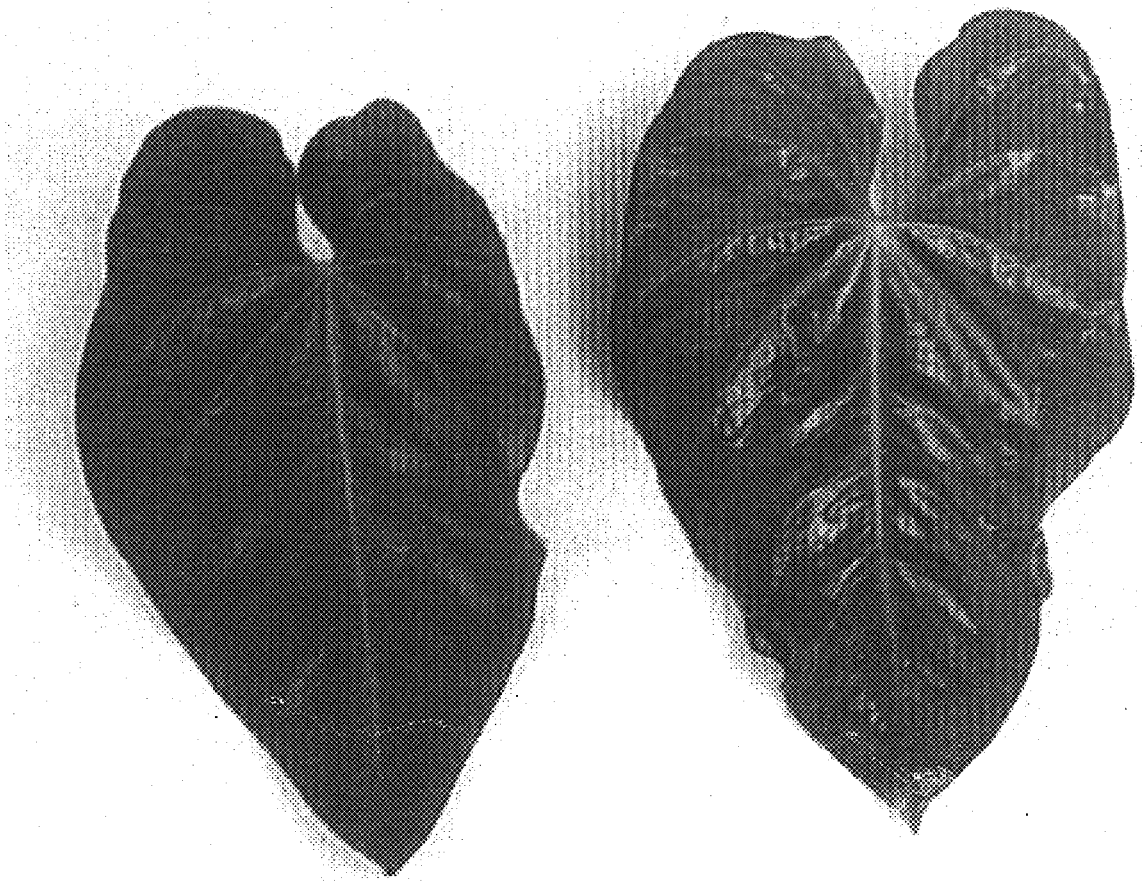

* * * * *